United States Patent
Tonks et al.

(10) Patent No.: US 12,215,128 B2
(45) Date of Patent: Feb. 4, 2025

(54) (PYRIDINYLMETHYL)BUTANEDIAMINE DERIVATIVES THAT CHELATE COPPER

(71) Applicants: COLD SPRING HARBOR LABORATORY, Cold Spring Harbor, NY (US); DEPYMED, INC., Farmingdale, NY (US)

(72) Inventors: Nicholas Tonks, Cold Spring Harbor, NY (US); Navasona Krishnan, Hawthorn Woods, IL (US); Andreas Grill, Saint James, NY (US)

(73) Assignees: Cold Spring Harbor Laboratory, Cold Spring Harbor, NY (US); Depymed, Inc., Farmingdale, NY (US)

( * ) Notice: Subject to any disclaimer, the term of this patent is extended or adjusted under 35 U.S.C. 154(b) by 924 days.

(21) Appl. No.: 17/261,313

(22) PCT Filed: Jul. 19, 2019

(86) PCT No.: PCT/US2019/042580
§ 371 (c)(1),
(2) Date: Jan. 19, 2021

(87) PCT Pub. No.: WO2020/018893
PCT Pub. Date: Jan. 23, 2020

(65) Prior Publication Data
US 2021/0261602 A1    Aug. 26, 2021

Related U.S. Application Data

(60) Provisional application No. 62/700,968, filed on Jul. 20, 2018, provisional application No. 62/855,031, filed on May 31, 2019.

(51) Int. Cl.
| | | |
|---|---|---|
| *C07D 213/38* | (2006.01) | |
| *C07D 401/12* | (2006.01) | |
| *C07J 43/00* | (2006.01) | |

(52) U.S. Cl.
CPC .......... *C07J 43/003* (2013.01); *C07D 213/38* (2013.01); *C07D 401/12* (2013.01)

(58) Field of Classification Search
CPC ............................ C07D 213/38; C07D 401/12
See application file for complete search history.

(56) References Cited

U.S. PATENT DOCUMENTS

| | | |
|---|---|---|
| 9,546,194 B2 | 1/2017 | McLane et al. |
| 2015/0099727 A1* | 4/2015 | McLane ............. C07J 41/005 |
| | | 552/521 |

FOREIGN PATENT DOCUMENTS

| | | |
|---|---|---|
| WO | 2019090331 A1 | 5/2019 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995. (Year: 1995).*

International Search Report and Written Opinion issued in PCT/US2019/042580 and mailed Nov. 5, 2019.

N. Krishnan et al., "DPM-1001 decreased copper levels and ameliorated deficits in a mouse of Wilson's disease", Gene & Development, Jun. 26, 2018, vol. 32, pp. 944-952.

N. Wilson et al., "A lipophilic copper (II) complex as an optical probe for intracellular detection of NO", Dalton Transactions, 2016, vol. 45, No. 45, pp. 18177-18182.

N. Krishnan et al., "A potent, selective and orally bioavailable inhibitor of the protein tyrosine phosphatase PTP1B improves insulin and leptin signaling in animal models", JBC Papers in Press, Dec. 7, 2017, Manuscrtip C117.819110.

* cited by examiner

*Primary Examiner* — Marcos L Sznaidman
(74) *Attorney, Agent, or Firm* — Heslin Rothenberg, Farley & Mesiti P.C.

(57) ABSTRACT

Compounds of formula:

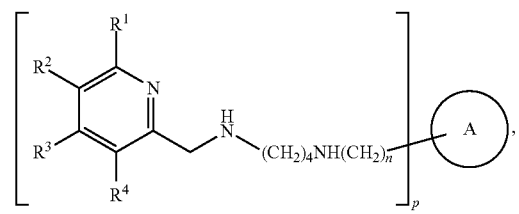

are described herein. The compounds selectively complex copper and are therefore useful both abiotically for measuring and detecting small amounts of copper and, in biological systems, for treating diseases associated with inappropriate copper levels, such as Wilson's disease and gastric cancer.

19 Claims, No Drawings

(PYRIDINYLMETHYL)BUTANEDIAMINE DERIVATIVES THAT CHELATE COPPER

CROSS REFERENCE TO RELATED APPLICATIONS

This application is a national phase filing under 35 U.S.C. § 371 of PCT International Application PCT/US2019/042580, filed Jul. 19, 2019. PCT/US2019/042580 claimed priority from U.S. provisional application 62/700,968, filed Jul. 20, 2018, and from U.S. provisional application 62/855,031, filed May 31, 2019. The contents of each of the prior applications are incorporated herein by reference in their entirety.

GOVERNMENT RIGHTS STATEMENT

This invention was made with Government support under grant numbers CA053840 and GM055989 awarded by the National Institutes of Health. The Government has certain rights in the invention.

FIELD OF THE INVENTION

The subject matter disclosed herein relates to compounds for complexing with copper ions and uses thereof. The compounds are $N^1$-(substituted)-$N^4$-(pyridin-2-ylmethyl)butane-1,4-diamines. As a consequence of their ability to selectively chelate copper, they are useful in the treatment of copper-related diseases and as inhibitors of copper-dependent enzymatic activity.

BACKGROUND OF THE INVENTION

Copper has been implicated in the regulation of signal transduction through control of the activity of kinases such as MEK, linking copper to the control of cell growth. Physiological levels of copper are under complex homeostatic control, including transporters that control influx and efflux, together with specialized chaperones that deliver the metal to its sites of action. Disruption of these homeostatic mechanisms is associated with a variety of disease states. Mutations in ATP7B, which functions in copper excretion, lead to accumulation of the metal resulting in Wilson's disease, a severe autosomal recessive disorder. The physical burden of the disease is felt in the liver, in particular, as this tissue expresses high levels of ATP7B. It begins with a presymptomatic period, during which copper accumulates in the liver. A variety of hepatic problems are encountered from enlargement of the liver, to hepatitis and cirrhosis, and even acute liver failure. Current treatment strategies depend on chelators that act as "de-coppering" agents, the goal of which is to decrease the level of the metal and to try to re-establish normal homeostasis. Unfortunately, penicillamine and trientine, which are the pharmacological agents that are used most frequently, are associated with severe adverse effects. Consequently, new potent and specific copper-chelators are needed for the treatment of Wilson's disease.

Disruption of copper homeostatic mechanisms is also linked to tumorigenesis and metastasis.

Selective copper chelators are also valuable in other fields, where precise measurement of low levels of copper is important, such as the production of radiometals [Dearling et al., Curr Radiopharm. 2017; 10 (1): 59-64.] In this regard, copper-chelating ligands can be coupled to fluorescein or other UV fluorescing moieties to produce reagents that combine high UV absorbance and high quantum yield with the ability to selectively chelate copper in the presence of other metal ions. Such materials can enable measurement of Cu(II) concentrations down to the ppm range.

SUMMARY OF THE INVENTION

In one aspect, the invention relates to compounds of formula I:

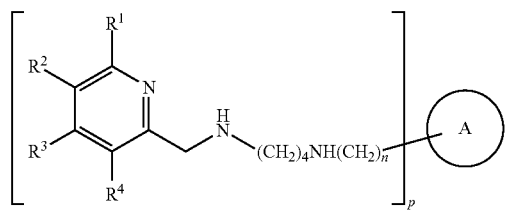

wherein $R^1$, $R^2$, $R^3$ and $R^4$ are chosen independently from hydrogen, $(C_1-C_6)$alkyl, $(C_1-C_6)$oxaalkyl, and $(C_1-C_6)$aminoalkyl, or two adjacent $R^1$, $R^2$, $R^3$ and $R^4$ may form a five-, six-, or seven-membered ring, said five-, six-, or seven-membered ring optionally substituted with one or two substituents chosen from halogen, cyano, hydroxy, $(C_1-C_6)$alkyl, $(C_1-C_6)$oxaalkyl, and $(C_1-C_6)$aminoalkyl;

A is a polycyclic ring system of up to five rings, optionally substituted with one or more substituents chosen from halogen, hydroxy, $(C_1-C_6)$alkyl, oxo, $(C_1-C_6)$oxaalkyl, carboxy, $(C_1-C_6)$alkoxycarbonyl, $(C_1-C_6)$alkoxycarbonyl$(C_1-C_6)$alkyl, carboxy$(C_1-C_6)$alkyl, amino, and $(C_1-C_6)$aminoalkyl;

n is zero or one; and p is one or two.

In another aspect, the invention relates to a method of chelating copper, comprising contacting a sample containing copper with a compound described above, whereby a complex between the compound and copper is formed.

In another aspect, the invention relates to treating cancer in a patient diagnosed with cancer, comprising administering to the patient a compound described above.

In another aspect, the invention relates to treating Wilson's Disease in a patient diagnosed with Wilson's Disease, comprising administering to the patient a compound described above.

DETAILED DESCRIPTION OF THE INVENTION

Disclosed herein are compounds that can form a complex with copper, or such compounds complexed with copper, and uses thereof. Such compounds may be formulated as pharmaceutical compositions and may be administered to a patient in need of medical treatment. For example, the compounds can be administered to a human or animal subject, or brought into contact with a sample of biological tissue or cells, or an abiotic sample, in order to form a complex of the compounds with copper in the solution. For example, the compound may be used to chelate copper, so as to prevent or reduce the binding of copper to other molecules in the sample.

The invention relates to compounds of Formula I:

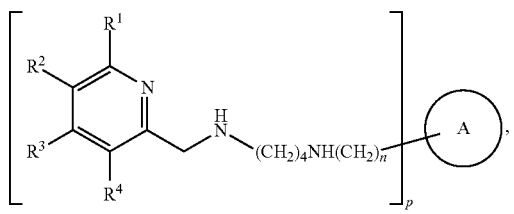

as described above. All of the compounds falling within the foregoing parent genus and its subgenera are useful as chelators of copper, but not all the compounds are novel. In particular, certain known species fall within the genus I, although utility in complexing copper has not yet been publicly disclosed for these species. In particular, compounds are disclosed in U.S. Pat. No. 9,365,608 and published US application 2105/0099727, in which A is a perhydrocyclopenta[a]phenanthrene of formula

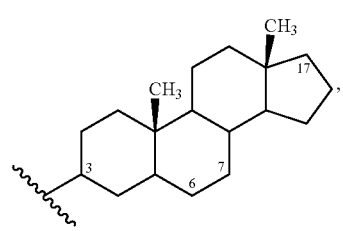 [SMILES: *C1CC[C@@]2(C)C(CCC3C4CCC[C@@]4(C)CCC32)C1]

$R^1$, $R^2$, $R^3$, and $R^4$ are all hydrogen, p is one, n is zero, and a substituent at 17 is —CH(CH$_3$)CH$_2$CH$_2$COOH, —CH(CH$_3$)CH$_2$CH$_2$COOCH$_3$, —CH(CH$_3$)CH$_2$CH$_2$CH(OSO$_3$H)CH(CH$_3$)$_2$,

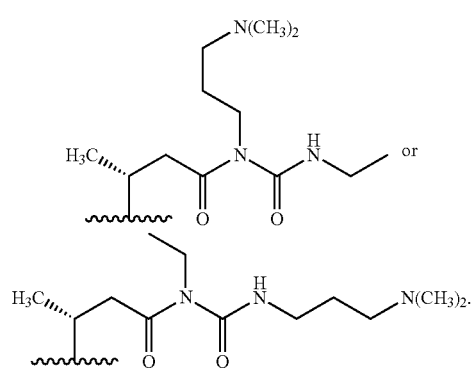

It may be found upon examination that compounds that have been excluded from the claims are patentable to the inventors in this application; it may also be found that additional species and genera not presently excluded are not patentable to the inventors in this application. In either case, the exclusion of species and genera in applicants' claims are to be considered artifacts of patent prosecution and not reflective of the inventors' concept or description of their invention. The invention, in a composition aspect, is all compounds of formula I except those that are in the public's possession.

In some embodiments, A is a polycyclic ring system chosen from

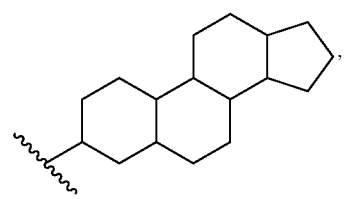

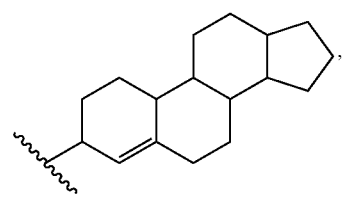

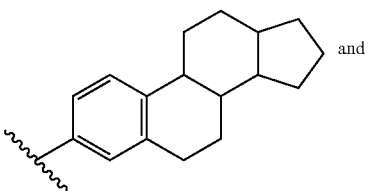

and

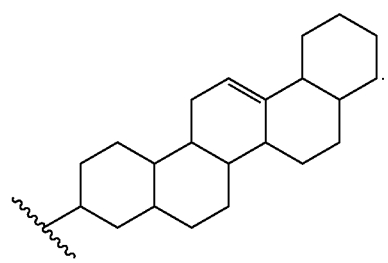

In some embodiments the polycyclic ring system A is a perhydrocyclopenta[a]phenanthrene of formula

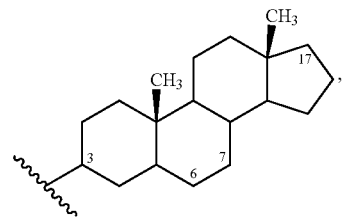 [SMILES: *C1CC[C@@]2(C)C(CCC3C4CCC[C@@]4(C)CCC32)C1]

substituted with hydroxyl at 6 or 7, in which a substituent at 17 is (C$_3$-C$_8$)alkyl.

In other embodiments p is one and A is a polycyclic ring system chosen from

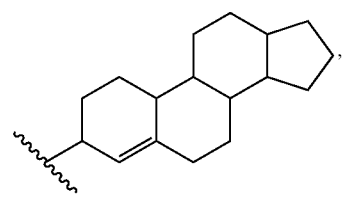

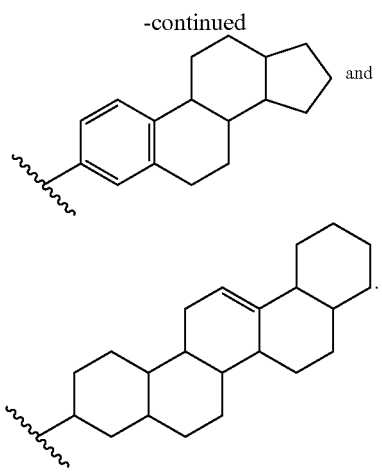

In other embodiments, A is a polycyclic ring system chosen from naphthalene, tetralin, decalin, phenanthrene, perhydrophenanthrene, octahydrophenanthrene, tetrahydrophenanthrene, indene, indane, fluorene, tetrahydrofluorene, tetrahydroanthracene, octahydroanthracene, and anthracene.

In other embodiments, A is a polycyclic ring system chosen from quinoline, isoquinoline, indole, carbazole, tetrahydroquinoline, tetrahydroisoquinoline, indoline, and isoindoline.

In other embodiments, p is one and A is

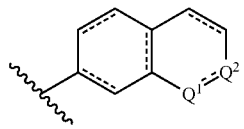

wherein dotted lines represent optional double bonds and $Q^1$ and $Q^2$ are independently chosen from carbon and nitrogen. For example, A may be naphthalene, tetralin, decalin, quinoline, isoquinoline, tetrahydroquinoline, or tetrahydroisoquinoline.

In any of the foregoing embodiments, the polycyclic ring system may be substituted with one or more substituents chosen from hydroxy, methyl, oxo, amino, $(C_1-C_6)$aminoalkyl, $(C_1-C_6)$oxaalkyl, carboxy, methoxycarbonyl, methoxycarbonyl$(C_1-C_6)$alkyl, and carboxy$(C_1-C_6)$alkyl. Alternatively, the polycyclic ring system may be unsubstituted.

In some embodiments, any adjacent pair of $R^1$, $R^2$, $R^3$ and $R^4$, taken together, form a benzene ring. In others, $R^1$, $R^2$, $R^3$, and $R^4$ are all hydrogen.

As disclosed herein, complexes of compounds of Formula I with copper have anti-tumor activities. For example, the compounds may be used in the treatment of breast cancer and gastrointestinal (GI) cancer. Some types of breast cancer cells express the protein HER2 (also known as receptor tyrosine-protein kinase erbB-2, CD340, proto-oncogene Neu, ERBB2), and expression of HER2 stimulates a cancer phenotype and tumor growth. PTP1B is over-expressed in certain HER2-positive breast cancer cells, and lack of PTP1B expression has been shown to prevent breast tumor development caused by over-expression of HER2. Triple-negative breast cancer cells have elevated levels of intracellular copper, and elevated levels of copper transporters responsible for importation of copper into cells. Contacting triple-negative breast cancer cells with a compound of Formula I reduces cellular copper levels.

Furthermore, some diabetes patients exhibit elevated copper levels. Similar to patients with Wilson's disease, elevated copper levels in diabetic patients can have cytotoxic effects and cause tissue or organ damage or dysfunction. The aforementioned method of treating patients having elevated copper levels by administering a compound of Formula I and thereby form a complex of such compound with copper, is also applicable to treatment of patients with diabetes.

Chelation refers to the binding of a compound to a metal ion with high affinity, forming a complex so that the metal remains bound to the compound rather than existing as a free metal ion in solution with the compound. Such complexes are formed at physiological conditions, such as when compounds of formula I are administered to cells in culture or to a mammalian animal or a human subject. Such complexes are also formed in abiotic solutions. An abiotic solution or sample is a sample that was not taken from a living subject or previously living subject and to which living cells or tissue or bodily fluids have not been purposefully added. An abiotic sample may be a solution from which copper removal may be desirable or measurement of copper levels may be desirable. Affinity is commonly measured and expressed as its inverse, a dissociation constant, $K_d$. Useful compounds exhibit a $K_d$ below 250 nM, and compounds described herein generally exhibit $K_d$ in the range from 25 to 250 nM.

A compound of Formula I may applied to any sample in which binding to or chelation of copper is desirable, or in which inhibition of enzymatic activity as disclosed herein is desired, or in which it may be desirable to test a potential role or importance of copper's availability. A sample may include, as described above, an abiotic sample. Or it may be a sample of cells, tissue, or bodily fluids taken or harvested from a living organism or previously living organism. A sample could also include a subject meaning an organism, including a human or nonhuman animal. For example, a subject may include a human or nonhuman animal in need of medical treatment. A sample could also include a biological solution, a suspension of biological material, or tissue, such as a solution or suspension of components taken from living cells or previously living cells, or from culture or tissue medial in which living cells or tissue were cultured, or may include bodily fluids, such as blood, saliva, cerebrospinal fluid, ascites, lymph, plasma, serum, mucous, or other bodily fluids or secretions. A biological sample could be a solution or suspension of organic molecules or other compounds produced by living cells. A sample that contains organic molecules synthesized other than by living cells, tissue, or organisms, such as by man-made methods, including synthetic copies of otherwise naturally occurring compounds, would not constitute a biological solution or suspension.

A pharmaceutical composition including a compound of Formula I includes, as a non-limiting example, such compound in a lyophilized or dry form such that dissolving such dry form in solvent, including upon oral administration to a subject, such compound would bind with copper as administered therewith in solution. Generally it is advantageous that the complex exhibit a Kd of 100 nM or less. Formulations for administration to a subject include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of a recipient or intended purpose of the administration. A formulation may conveniently be presented in unit dosage form and may be prepared by any of the methods well known in the art of pharmacy. Methods may include a step of bringing into association a compound of Formula I or a pharmaceutically acceptable salt thereof ("active ingredient") with a carrier which constitutes one or more accessory ingredients. In general, formulations may be prepared by uniformly and intimately bringing into association an active ingredient with liquid carriers or finely divided solid carriers or both and then, if necessary, shaping the product into the desired formulation.

Formulations of the present disclosure suitable for oral administration may be presented as discrete units such as capsules, cachets or tablets each containing a predetermined amount of an active ingredient; as a powder or granules; as a solution or a suspension in an aqueous liquid or a non-aqueous liquid; or as an oil-in-water liquid emulsion or a water-in-oil liquid emulsion. A compound of Formula I may also be presented as a bolus, electuary or paste. For oral or other administration, a compound of Formula I may be suspended in a solution, or dissolved in a solvent, such as alcohol, DMSO, water, saline, or other solvent, which may be further diluted or dissolved in another solution or solvent, and may or may contain a carrier or other excipient in some examples.

Formulations for parenteral or other administration include aqueous and non-aqueous sterile injection solutions which may contain anti-oxidants, buffers, bacteriostats and solutes which render a formulation isotonic with the blood of the intended recipient. Formulations for parenteral or other administration also may include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of a compound of Formula I to polymer and the nature of the particular polymer employed, the rate of a compound of Formula I release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

A compound of Formula I formulation may include different types of carriers depending on whether it is to be administered in solid, liquid or aerosol form, and whether it needs to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990.

The term "pharmaceutically acceptable salt" refers to salts prepared from pharmaceutically acceptable non-toxic acids or bases including inorganic acids and bases and organic acids and bases. Unless otherwise specified, reference herein to a compound of Formula I, or to any such compound in particular, includes reference to a pharmaceutically acceptable salt thereof. When the compounds of the present disclosure are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, betulinic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, ursolic and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

As used herein, the term "effective amount" means an amount of a compound of Formula I pharmaceutical agent that may elicit a biological or medical response of a cell, tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula I, as well as salts, solvates, and physiological functional derivatives thereof, may be administered as the raw chemical. Additionally, the active ingredient may be presented as a pharmaceutical composition.

Pharmaceutical compositions of the present invention include an effective amount of a compound of Formula I and optionally one or more additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains a compound of Formula I and optionally one or more additional active ingredient will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

The following examples are intended to illustrate particular embodiments of the present disclosure, but are by no means intended to limit the scope thereof.

Compounds of the genus I may be prepared by reductive amination of tert-butyl (4-oxobutyl) (pyridin-2-ylmethyl) carbamate (4) with the appropriate amine

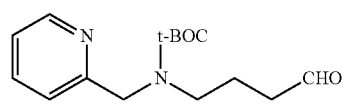
(4)

or $N^1$-(pyridin-2-ylmethyl) butane-1,4-diamine (8) with the appropriate aldehyde.

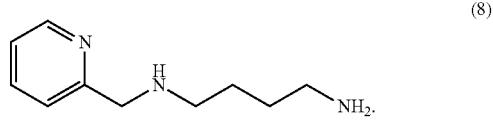 [SMILES: NCCCCNCc1ccccn1]
(8)

For example, compounds in which n is zero or one may be made by the general method:

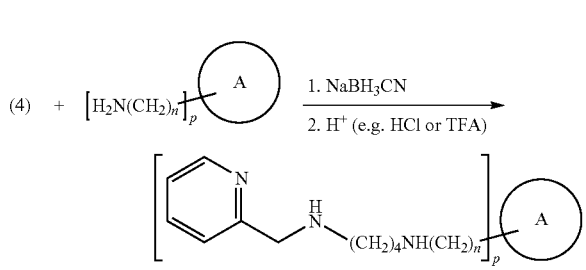

Alternatively, compounds in which n is one may be made by the general method:

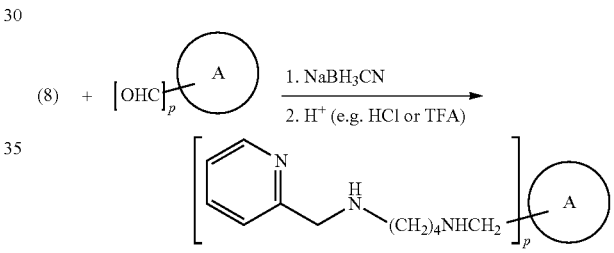

and compounds in which n is zero and A is not fully aromatic can be made analogously from ketonic A's, e.g. tetralones and decalones.

The tert-butyl (4-oxobutyl)(pyridin-2-ylmethyl)carbamate (4) is prepared by either Scheme 1a or Scheme 1b:

Scheme 1a

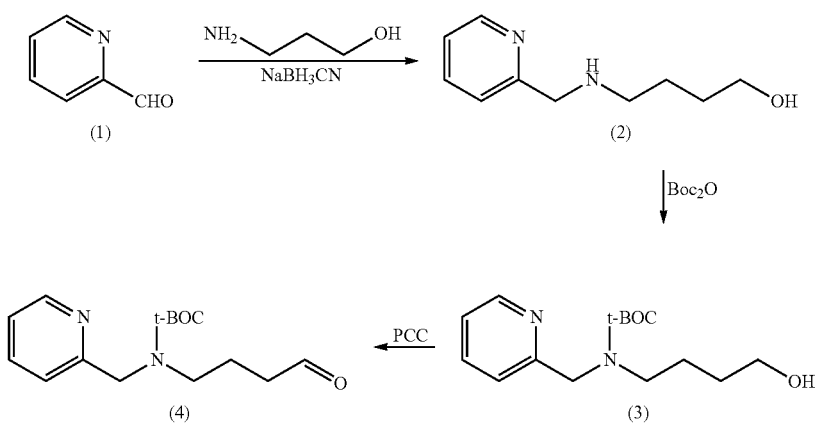

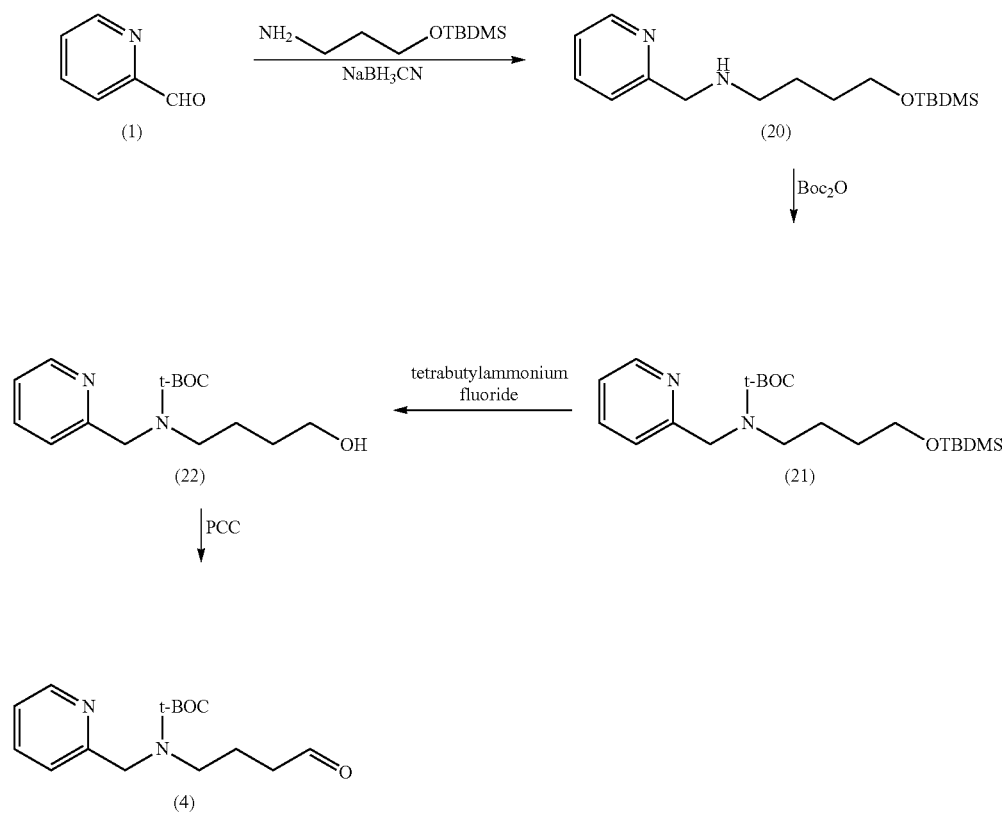
$N^1$-(Pyridin-2-ylmethyl) butane-1,4-diamine (8) is prepared by Scheme 2:
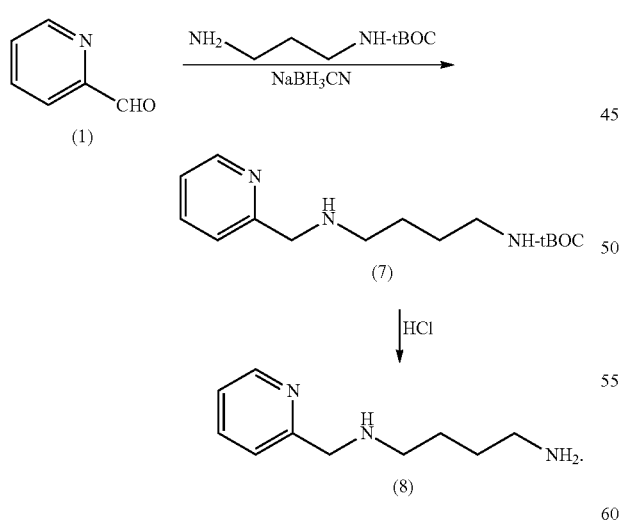
Compounds in which $R^1$, $R^2$, $R^3$ and/or $R^4$ is other than hydrogen may be made by starting with the appropriately substituted pyridine-2-carboxaldehyde.

Examples of the above illustrated syntheses are:
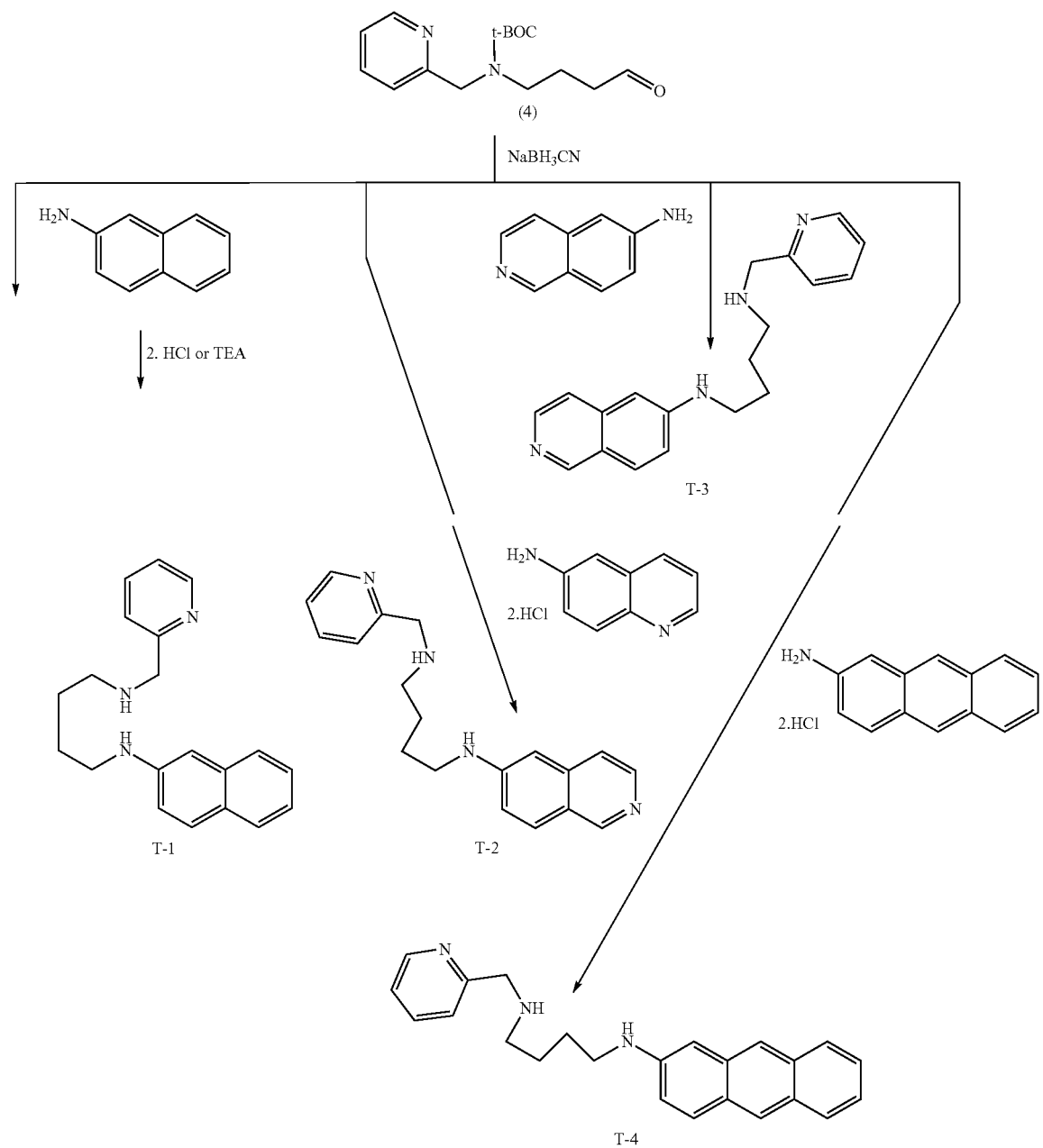
Scheme 3

-continued
Scheme 4
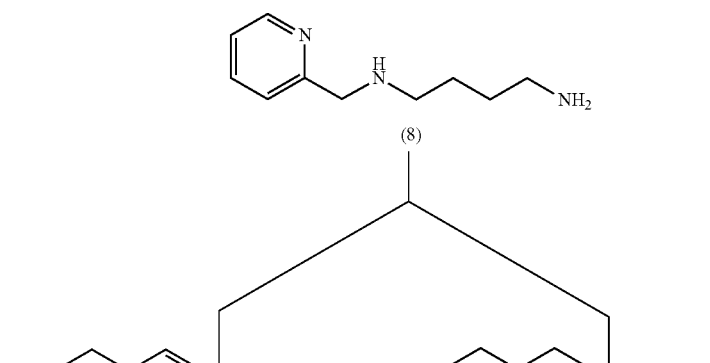
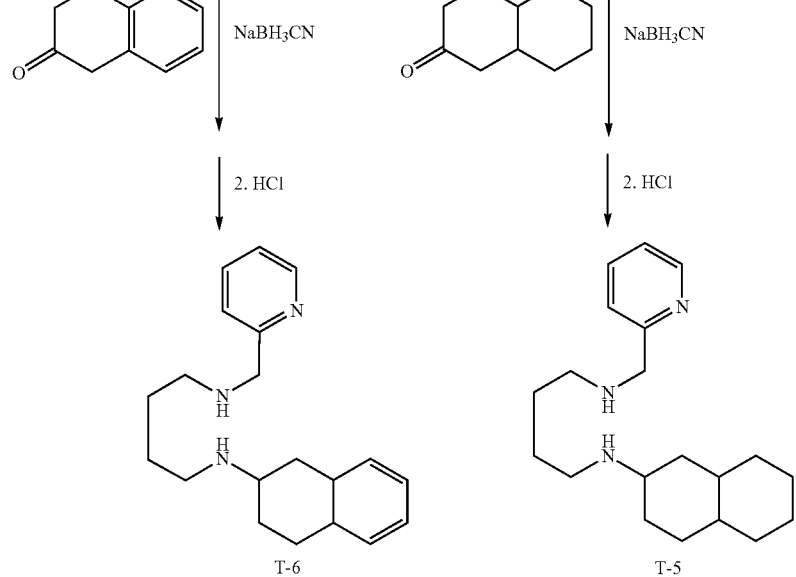
Scheme 5
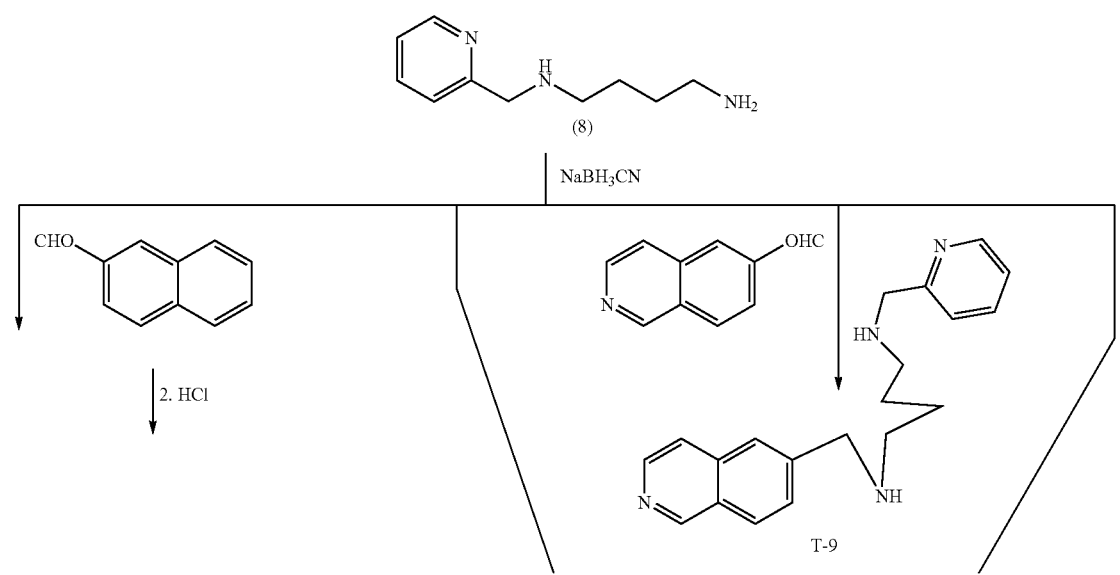

In similar fashion, the corresponding compound to T-7 in which p is 2 may be made from commercially available 2,6-naphthalenedicarboxaldehyde.

Compounds in which A is a substituted perhydrocyclopenta[a]phenanthrene may be made by the following general scheme 6:

Scheme 6

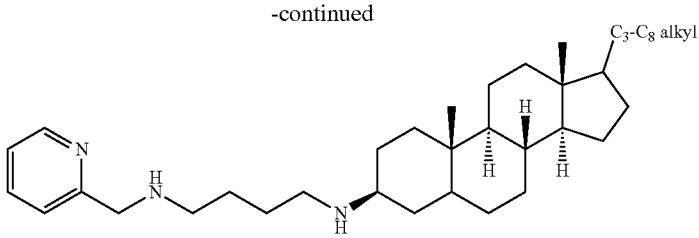

+

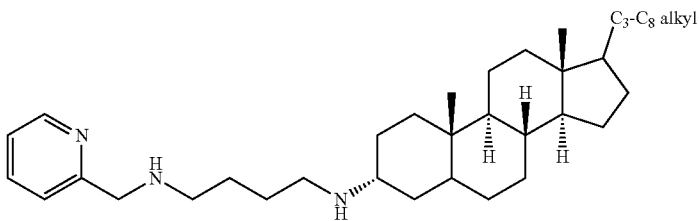

In a specific embodiment (C₃-C₈)alkyl is —(CH)(CH₂)₃CH(CH₃)₂ and the products are:

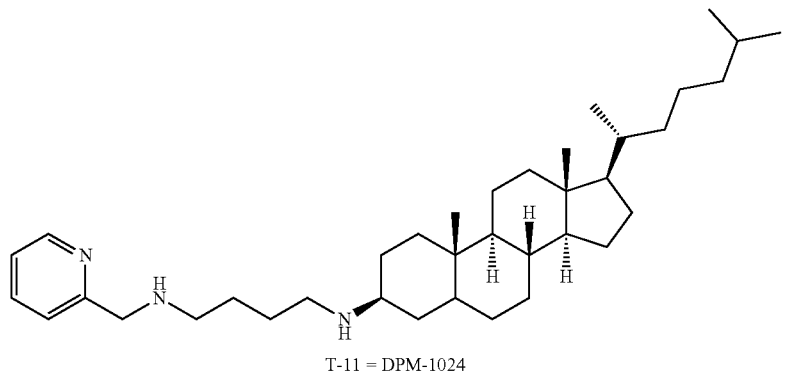

T-11 = DPM-1024

+

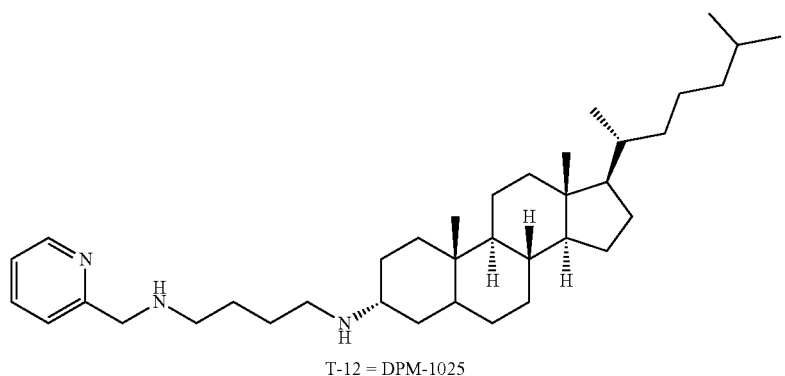

T-12 = DPM-1025

Preparation of 8:

To a solution of picolinaldehyde (5.0 g, 46.7 mmol) in CH₂Cl₂ (300 mL) was added tert-butyl (4-aminobutyl) carbamate (8.8 g, 46.74 mmol) followed by NaB(OAc)₃H (19.8 g, 93. 42 mmol) under a nitrogen atmosphere. The mixture was stirred at room temperature for 5 h. The reaction mixture was poured onto saturated NaHCO₃ solution (300 mL), and stirred for 10 min. The organic layer was separated, washed with saturated NaHCO₃ solution, brine and dried over anhydrous Na2SO4 before filtration and evaporation. The crude product was purified by silica gel flash chromatography eluting with 5-10% MeOH—CH₂Cl₂ to obtain 7 (6.9 g, 53%) as a yellow oil. TLC: Rf=0.4 (Silica gel, MeOH: CH2Cl2, 10:90). ¹H-NMR (300 MHz, CDCl₃) δ 8.54 (m, 1H, H-6), 7.64 (m, 1H, H-4), 7.20 (m, 1H, H-3), 7.18-7.13 (m, 1H), 3.89 (s, 2H, —CH₂N—), 3.2-3.05 (m, 2H, —CH₂NHBoc), 2.67 (t, 2H, —CH₂NH), 1.55-1.53 (m, 4H, —CH2-CH2-), 1.42 (s, 9H, —C(CH₃)₃). APCI+=280.

To a solution of 7 (6.9 g, 24.69 mmol) in CH₂Cl₂ (60 mL) at 0° C. was added TFA:CH₂Cl₂ (1:1, 40 mL) over 30 min at 0° C. The mixture was allowed to warm to room temperature, stirred overnight, and concentrated on a rotary evaporator along with toluene (5×100 mL) as cosolvent. The crude product was dissolved in water and lyophilized overnight to get a brown oil which was stirred with EtOAc (500 mL). The solid which separated out was filtered, washed with EtOAc and dried under vacuum to obtain 8 (8.2 g, 64%) as a white solid. 1H NMR (300 MHZ, CD₃OD) δ 8.66-8.62 (m, 1H, H-6), 7.91-7.82 (m, 1H, H-4), 7.48-7.39 (m, 2H, H-3, H-5), 4.38 (s, 2H, —CH₂N—), 3.2-3.12 (m, 2H, —CH₂N), 3.03-2.94 (m, 2H, —CH2N), 1.91-1.70 (m, 4H, —CH₂—CH₂). APCI+=180.

Preparation of T-11 and T-12:

To a mixture of dihydrocholesterone (0.71 mmole) and 9 (160 mg, 0.35 mmole) in CH₃OH:THF (1:1, 8 mL) is added 3 Å molecular sieves (1 g) followed by DIPEA (0.55 g, 4.26 mmol) and the mixture is stirred overnight. If reaction is incomplete, a further 1 g of 4 Å molecular sieves is added and the mixture was stirred for 7 h more. Na BH₃CN is added (71 mg, 1.13 mmol). The mixture is stirred at RT for 2 d. The reaction mixture is filtered through a pad of Celite, and washed with dichloromethane and methanol. The filtrate is concentrated to provide the crude product, which is redissolved in dichloromethane, washed with water, 5% NaOH solution; the aqueous phase is re-extracted with dichloromethane and the combined organic phase washed with brine, dried (Na₂SO₄) and the solvent removed under reduced pressure to isolate the crude product. This material may be purified by FCC using 1-10% MeOH/CHCl₃ and 1-2% NH₃ in MeOH to isolate 3α-isomer (T-11) and 3β-isomer (T-12).

In other specific embodiments A is a substituted perhydrocyclopenta[a]phenanthrene with a hydroxyl at C-7 and (C₃-C₈)alkyl at 17, as shown in Schemes 7 and 8 for examples T-13, T-14, T-15 and T-16.

Scheme 7

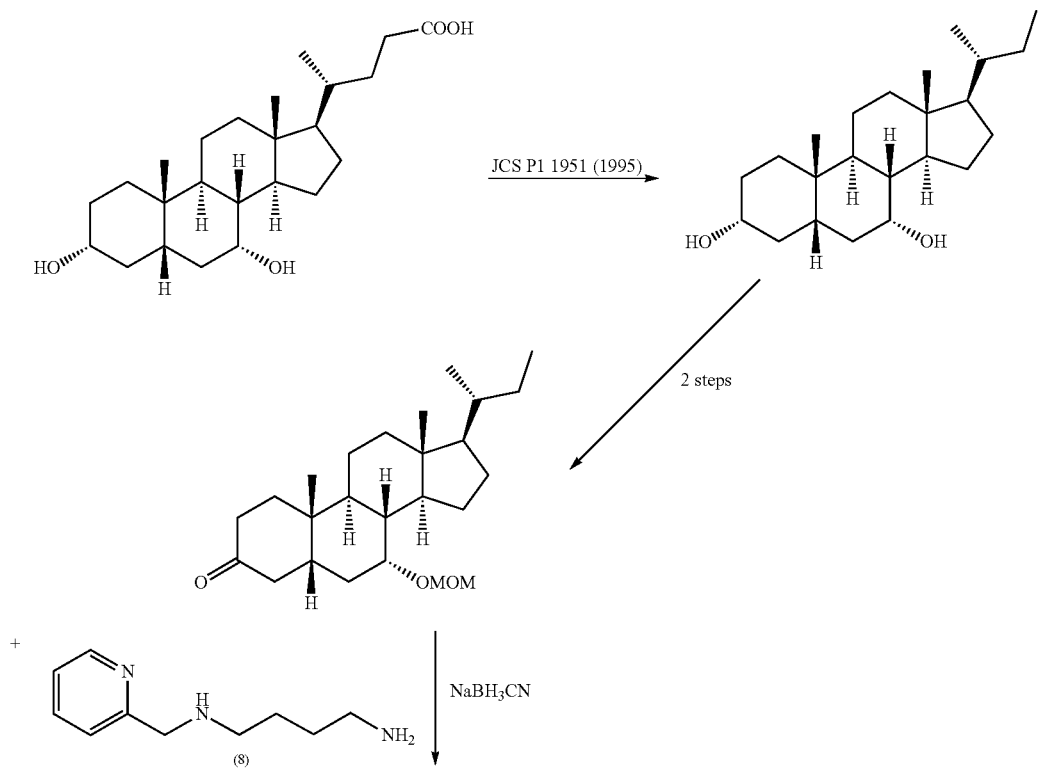

-continued
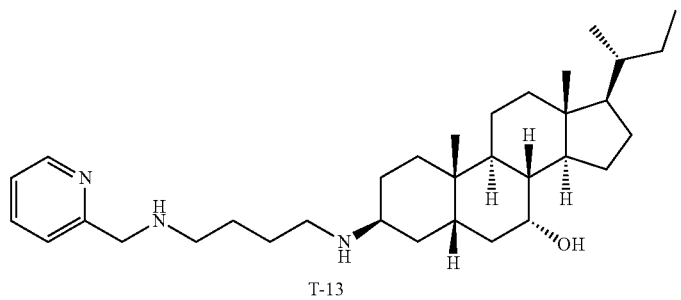
T-13
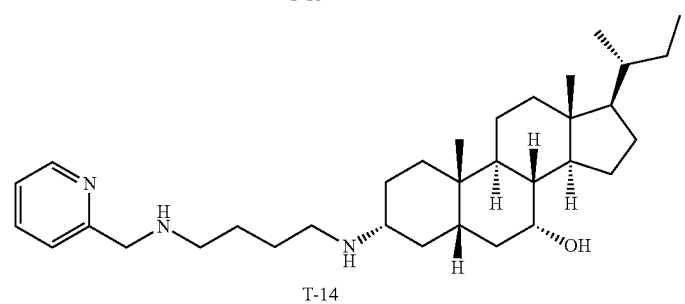
T-14
Scheme 8
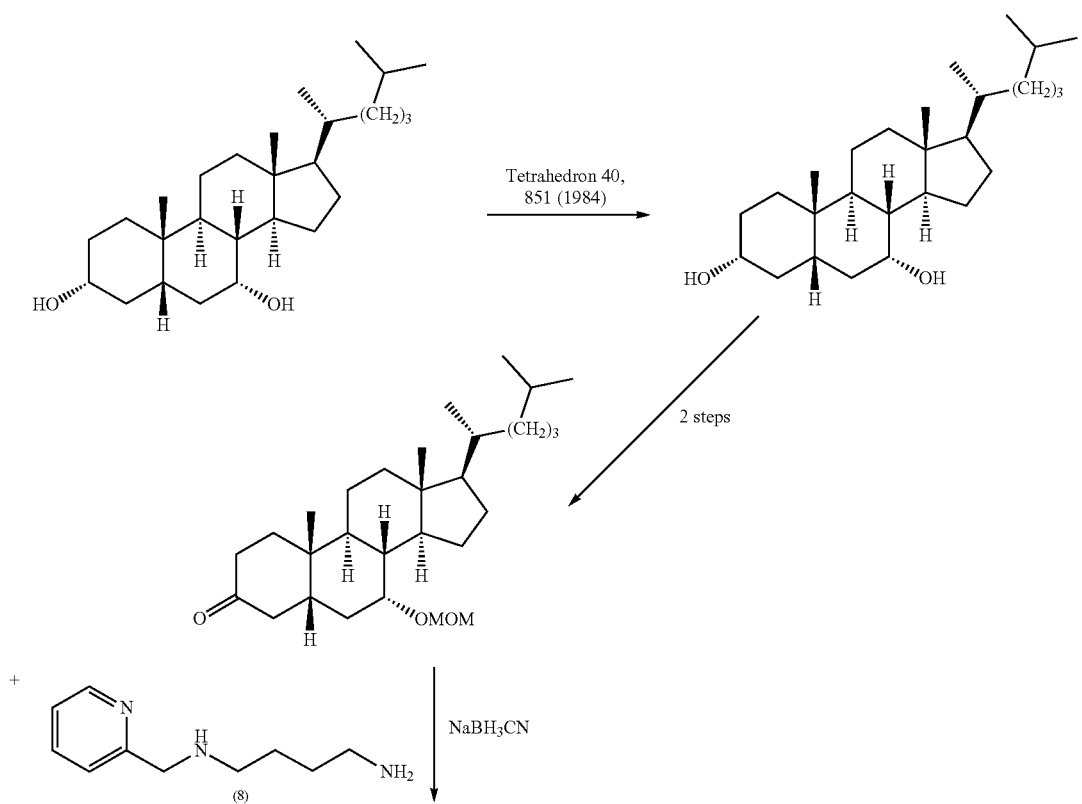

-continued
↓ deprotect
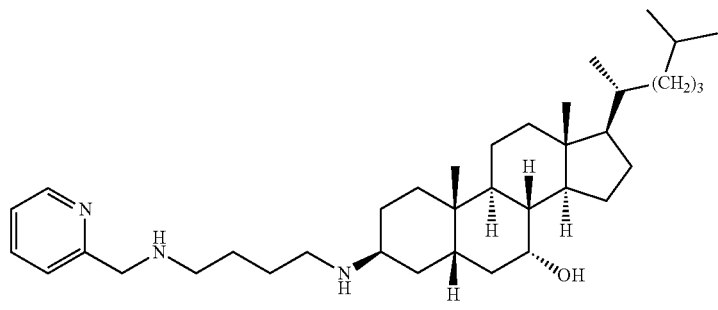
T-15 = DPM-1024
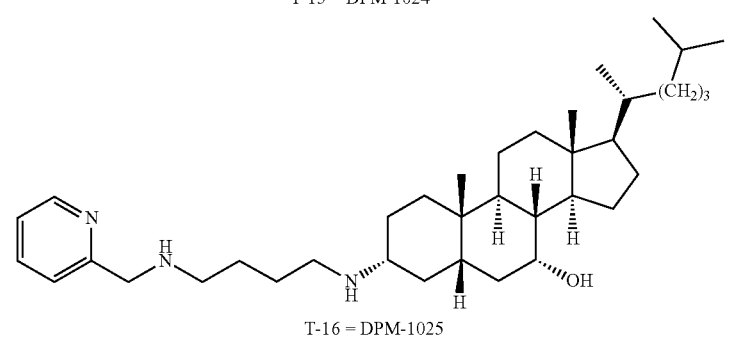
T-16 = DPM-1025
Employing the syntheses above, the following compounds were prepared:
| Compound ID | Structure | Cu-64 binding $K_d$ |
|---|---|---|
| DPM-1011 | 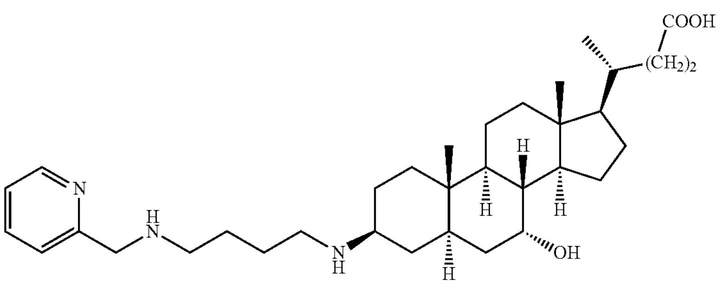 | |
| DPM-1012 | 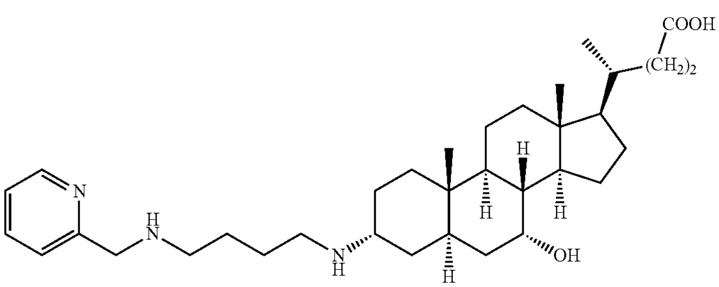 | |

-continued

| Compound ID | Structure | Cu-64 binding $K_d$ |
|---|---|---|
| DPM-1013 | 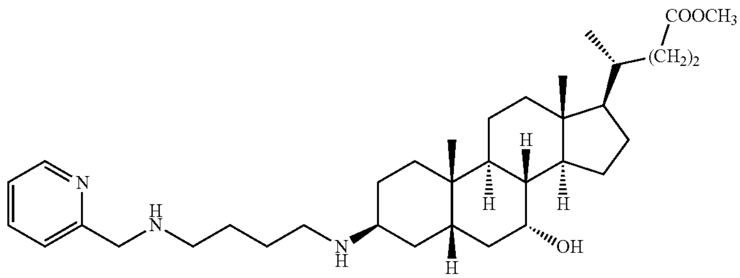 | 24 nM |
| DPM-1014 | 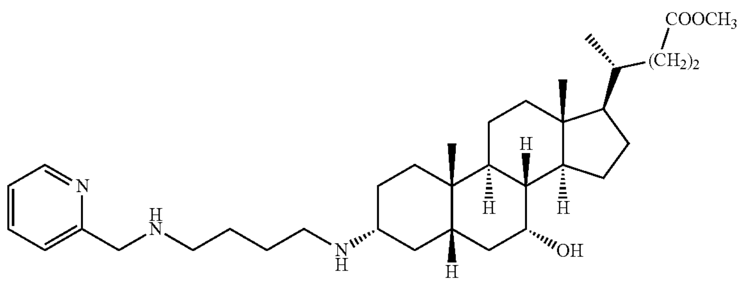 | 27 nM |
| DPM-1015 | 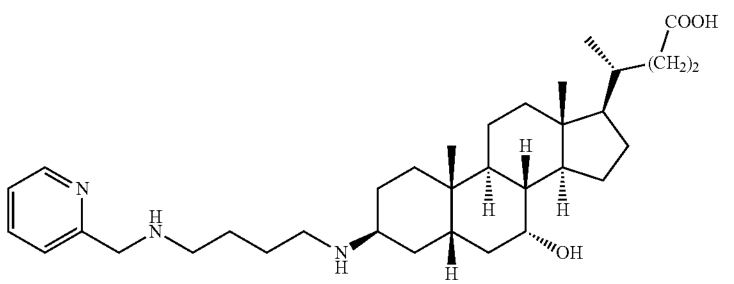 | 27 nM |
| DPM-1016 | 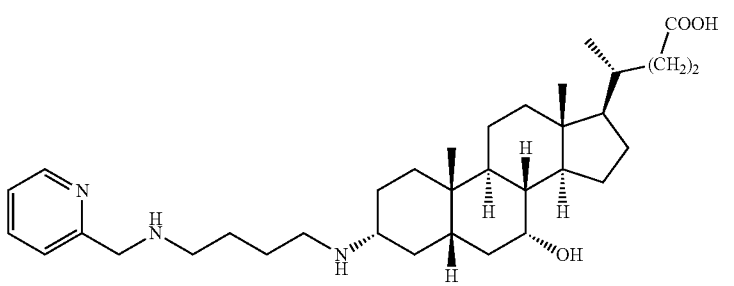 | 27 nM |
| DPM-1017 | 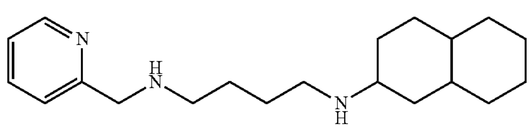 [SMILES: c1ccc(CNCCCCNC2CCC3CCCCC3C2)nc1] | |
| DPM-1018 | 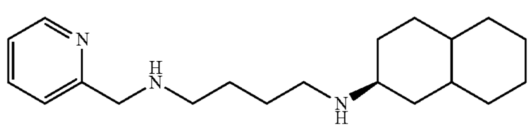 [SMILES: c1ccc(CNCCCCN[C@H]2CCC3CCCCC3C2)nc1] | |
| DPM-1019 | 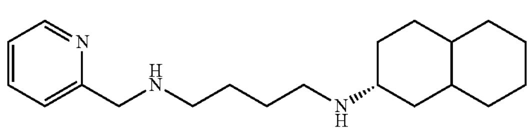 [SMILES: c1ccc(CNCCCCN[C@@H]2CCC3CCCCC3C2)nc1] | |

| Compound ID | Structure | Cu-64 binding K$_d$ |
|---|---|---|
| DPM-1020 | 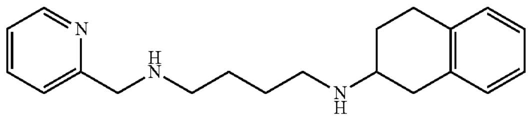 [SMILES: c1ccc(CNCCCCNC2CCc3ccccc3C2)nc1] | |
| DPM-1021 | 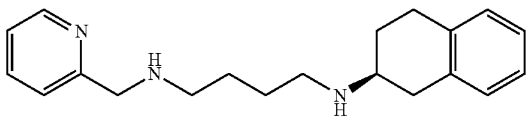 [SMILES: c1ccc(CNCCCCN[C@H]2CCc3ccccc3C2)nc1] | |
| DPM-1022 | 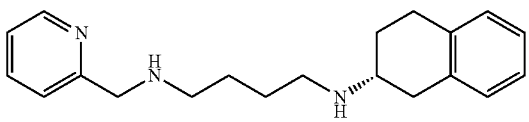 [SMILES: c1ccc(CNCCCCN[C@@H]2CCc3ccccc3C2)nc1] | |
| DPM-1023 | 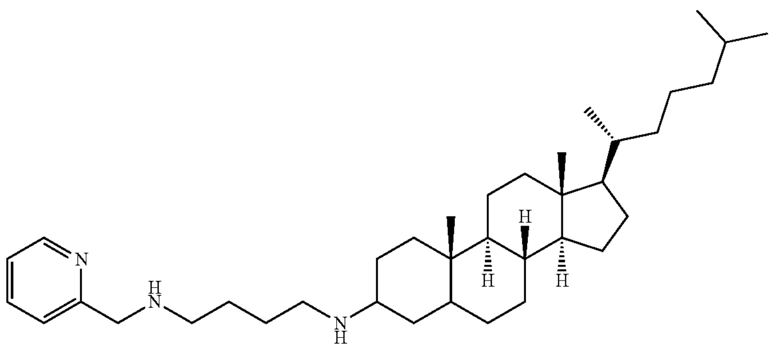 | 3.6 |
| DPM-1024 | 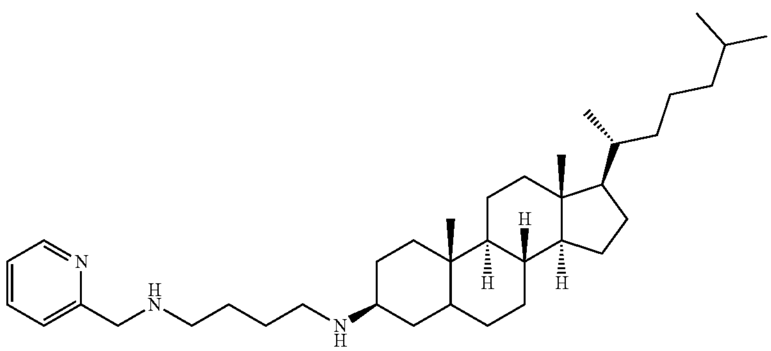 | |
| DPM-1025 | 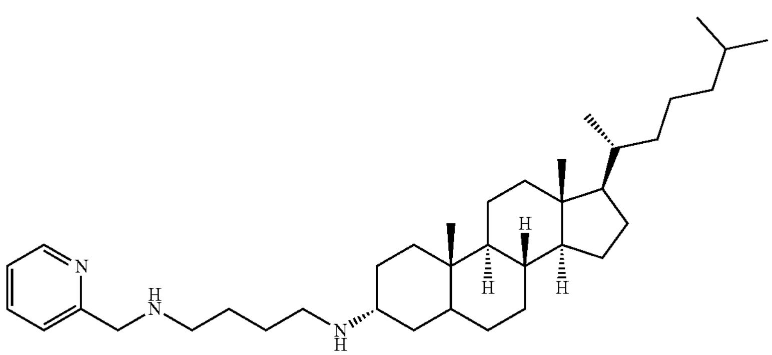 | |
| DPM-1026 | 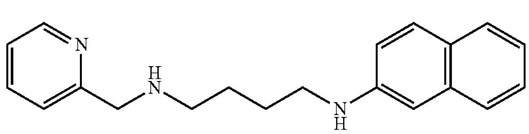 [SMILES: c1ccc(CNCCCCNc2ccc3ccccc3c2)nc1] | 21 nM |

| Compound ID | Structure | Cu-64 binding $K_d$ |
|---|---|---|
| DPM-1027 | 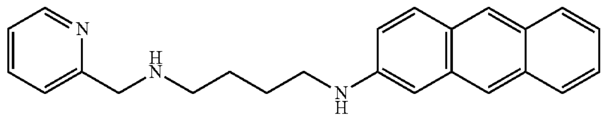 [SMILES: c1ccc(CNCCCCNc2ccc3cc4ccccc4cc3c2)nc1] | |
| DPM-1028 | 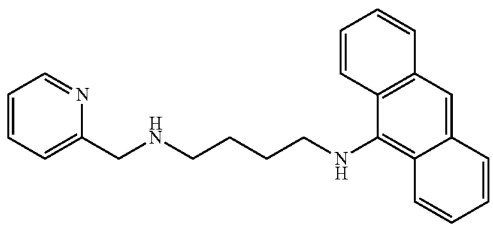 [SMILES: c1ccc(CNCCCCNc2c3ccccc3cc3ccccc23)nc1] | 25 nM |
| DPM-1031 | 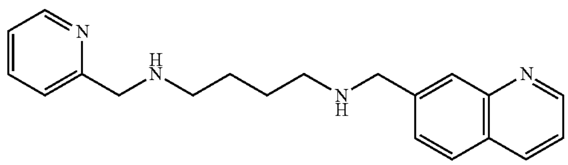 [SMILES: c1ccc(CNCCCCNCc2ccc3cccnc3c2)nc1] | 24 nM |
| DPM-1032 | 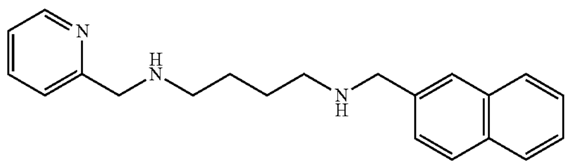 [SMILES: c1ccc(CNCCCCNCc2ccc3ccccc3c2)nc1] | 21 nM |
| DPM-1033 | 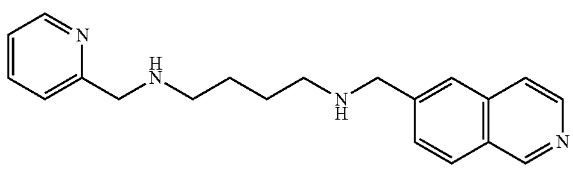 [SMILES: c1ccc(CNCCCCNCc2ccc3cnccc3c2)nc1] | 29 nM |
| O-10634 | 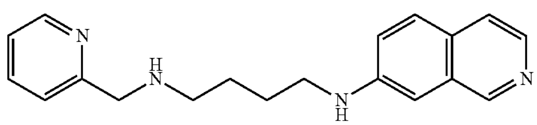 [SMILES: c1ccc(CNCCCCNc2ccc3ccncc3c2)nc1] | 12 nM |
| O-10635 | 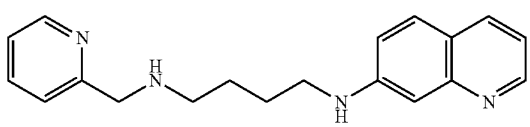 [SMILES: c1ccc(CNCCCCNc2ccc3cccnc3c2)nc1] | 17 nM |

Copper-Binding Assays:

Direct binding assays are performed using radiolabelled copper (64 $Cu^{2+}$). Varying concentrations of radiolabeled copper (0-100 nM) are incubated with test compound (100 nM). Excess copper is removed by running the samples through a desalting column. The amount of metal bound to the compound was quantitated directly by scintillation counting. In general, compounds of formula I will have binding constants ($K_d$) in the sub-micromolar range, and their selectivity for copper in the presence of other divalent metals (e.g. nickel, manganese, magnesium and cobalt) will be exhibited as at least a 100-fold lower $K_d$ for copper than for the other metals. Except for the subgenus in which A is quinoline or isoquinoline, the compounds of the invention bind copper selectively and do not appear to bind cobalt, manganese, iron or magnesium ions at the concentrations tested (up to eight equivalents excess of metal salt). Some samples were additionally tested against silver, molybdenum, antimony, nickel, chromium, zinc, calcium and ruthenium, and were found not to bind at levels that showed clear binding to copper.

Compounds described herein lower copper levels in animal models of Wilson's disease. The TX mouse is a naturally occurring genetic and phenotypic model of Wilson's disease. A Gly to Asp substitution (G775D) renders the ATP7B protein dysfunctional and results in copper accumulation. This has been used widely as a model to understand the human disease. TX and wild-type mice exhibit different longevities. Survival in TX and wild-type mice treated with test compound or saline may be assessed. Wild-type mice treated with saline or test compound have a higher survival rate at one year of age.

Tissue copper levels can be assessed by two separate methods. Liver tissue is excised from wild-type and TX mice that have been treated with saline or test compound, then fixed and stained with rhodanine, a dye that stains for copper-binding proteins. The signal detected in liver samples obtained from saline- or test compound-treated wild-type mice is significantly reduces compared to saline-treated TX mice, in which bright staining with the dye is observed, indicative of elevated copper levels. In contrast, greatly reduced or no staining for rhodanine will be observed in liver samples obtained from mice treated with compounds of the invention.

Although preferred embodiments have been depicted and described in detail herein, it will be apparent to those skilled in the relevant art that various modifications, additions, substitutions, and the like can be made without departing from the spirit of the present disclosure and these are therefore considered to be within the scope of the present disclosure as defined in the claims that follow.

The invention claimed is:

1. A compound of formula:

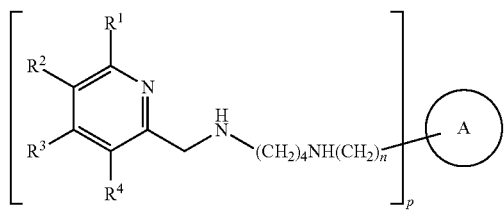

wherein $R^1$, $R^2$, $R^3$ and $R^4$ are chosen independently from hydrogen, $(C_1-C_6)$alkyl, $(C_1-C_6)$oxaalkyl, and $(C_1-C_6)$aminoalkyl, or two adjacent $R^1$, $R^2$, $R^3$ and $R^4$ may form a five-, six-, or seven-membered ring, said five-, six-, or seven-membered ring optionally substituted with one or two substituents chosen from halogen, cyano, hydroxy, $(C_1-C_6)$alkyl, $(C_1-C_6)$oxaalkyl, and $(C_1-C_6)$aminoalkyl;

A is a polycyclic ring system chosen from one of the following ring systems:

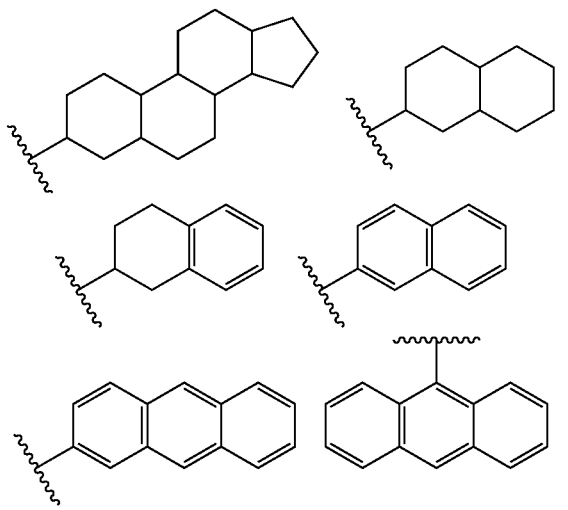

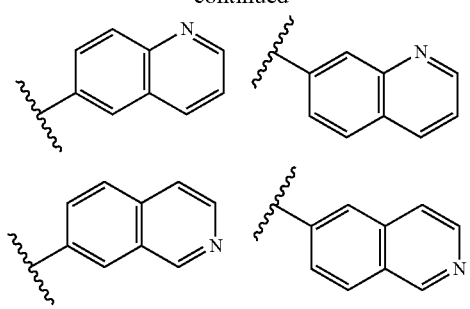

said rings optionally substituted with one or more substituents chosen from halogen, hydroxy, $(C_1-C_6)$alkyl, oxo, $(C_1-C_6)$oxaalkyl, carboxy, $(C_1-C_6)$alkoxycarbonyl, $(C_1-C_6)$alkoxycarbonyl$(C_1-C_6)$alkyl, carboxy$(C_1-C_6)$alkyl, amino, and $(C_1-C_6)$aminoalkyl;

n is zero or one; and p is one or two;

with the proviso that, when $R^1$, $R^2$, $R^3$, and $R^4$ are all hydrogen, p is one, and n is zero, the polycyclic ring system A is not a perhydrocyclopenta[a]phenanthrene of formula

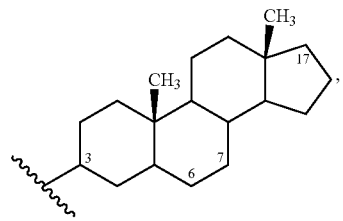 [SMILES: *C1CC[C@@]2(C)C(CCC3C4CCC[C@@]4(C)CCC32)C1]

attached at the 3-position as shown, in which a substituent at 17 is —CH(CH$_3$)CH$_2$CH$_2$COOH, —CH(CH$_3$)CH$_2$CH$_2$COOCH$_3$, —CH(CH$_3$)CH$_2$CH$_2$CH(OSO$_3$H)CH(CH$_3$)$_2$,

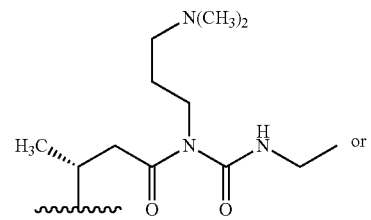

or

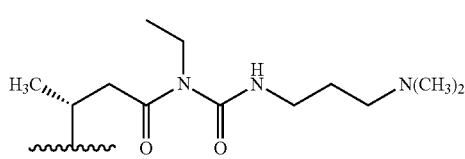

regardless of the remaining substitutions of the ring.

2. A compound according to claim 1 wherein p is one and A is

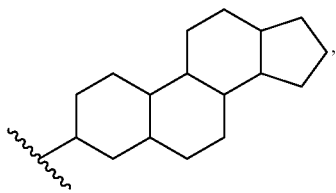 [SMILES: *C1CCC2C(CCC3C4CCCC4CCC23)C1]

3. A compound according to claim 2 wherein the polycyclic ring system A is a perhydrocyclopenta[a]phenanthrene of formula

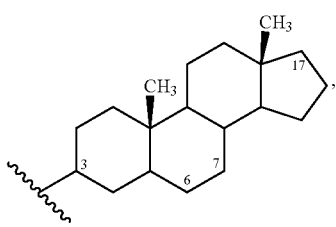 [SMILES: *C1CC[C@@]2(C)C(CCC3C4CCC[C@@]4(C)CCC32)C1]

substituted with hydroxyl at 6 or 7, in which a substituent at 17 is $(C_3-C_8)$alkyl.

4. A compound according to claim 1 wherein A is a polycyclic ring system chosen from naphthalene, tetralin, decalin, and anthracene.

5. A compound according to claim 4 wherein p is one.

6. A compound according to claim 4 wherein p is two.

7. A compound according to claim 1 wherein A is a polycyclic ring system chosen from quinoline, isoquinoline.

8. A compound according to claim 7 wherein p is one.

9. A compound according to claim 7 wherein p is two.

10. A compound according to claim 1 wherein p is one and A is

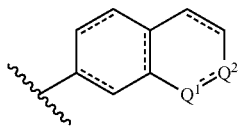

wherein dotted lines represent optional double bonds and $Q^1$ and $Q^2$ are independently chosen from carbon and nitrogen.

11. A compound according to claim 2 wherein said polycyclic ring system is substituted with one or more substituents chosen from hydroxy, methyl, oxo, amino, $(C_1-C_6)$aminoalkyl, $(C_1-C_6)$oxaalkyl, carboxy, methoxycarbonyl, methoxycarbonyl$(C_1-C_6)$alkyl, and carboxy$(C_1-C_6)$alkyl.

12. A compound according to claim 2 wherein said polycyclic ring system is unsubstituted.

13. A compound according to claim 1 wherein any adjacent pair of $R^1$, $R^2$, $R^3$ and $R^4$, taken together, form a benzene ring.

14. A compound according to claim 1 wherein $R^1$, $R^2$, $R^3$, and $R^4$ are all hydrogen.

15. A compound according to claim 1 wherein n is one.

16. A compound according to claim 1 wherein n is zero.

17. A compound according to claim 1 wherein A is other than quinoline or isoquinoline.

18. A method of chelating copper, comprising contacting a sample containing copper with a compound according to claim 1, whereby a complex between said compound and copper is formed.

19. A pharmaceutical composition comprising a pharmaceutically acceptable vehicle and a compound according to claim 1.

* * * * *